US008582094B1

(12) United States Patent
Shortt et al.

(10) Patent No.: US 8,582,094 B1
(45) Date of Patent: Nov. 12, 2013

(54) SYSTEMS AND METHODS FOR INSPECTING SPECIMENS INCLUDING SPECIMENS THAT HAVE A SUBSTANTIALLY ROUGH UPPERMOST LAYER

(75) Inventors: David Shortt, Milpitas, CA (US); Stephen Biellak, Sunnyvale, CA (US); Christian Wolters, Campbell, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 2209 days.

(21) Appl. No.: 11/110,383

(22) Filed: Apr. 20, 2005

(51) Int. Cl.
*G01N 21/00* (2006.01)
*G01J 4/00* (2006.01)

(52) U.S. Cl.
USPC .................. 356/237.1; 356/337; 356/364

(58) Field of Classification Search
USPC ............. 356/445, 600, 239.1, 239.3, 356/237.1–237.6, 364
See application file for complete search history.

(56) References Cited

U.S. PATENT DOCUMENTS

| | | | | |
|---|---|---|---|---|
| 4,286,843 A | * | 9/1981 | Reytblatt | 359/489 |
| 4,898,471 A | * | 2/1990 | Vaught et al. | 356/394 |
| 5,493,123 A | * | 2/1996 | Knollenberg et al. | 250/372 |
| 5,585,918 A | * | 12/1996 | Takeuchi et al. | 356/237.1 |
| 6,034,776 A | | 3/2000 | Germer et al. | |
| 6,177,993 B1 | * | 1/2001 | Sommargren | 356/337 |
| 6,201,601 B1 | | 3/2001 | Vaez-Iravani et al. | |
| 6,271,916 B1 | | 8/2001 | Marxer et al. | |
| 6,538,730 B2 | | 3/2003 | Vaez-Iravani et al. | |
| 6,943,941 B2 | | 9/2005 | Flagello et al. | |
| 7,221,501 B2 | | 5/2007 | Flagello et al. | |
| 2004/0246476 A1 | * | 12/2004 | Bevis et al. | 356/237.5 |

OTHER PUBLICATIONS

Rice, "Reflection of Electromagnetic Waves from Slightly Rough Surfaces," Communications in Pure and Applied Mathematics, vol. 4, 1951, pp. 351-378.
Church et al., "Relationship between Surface Scattering and Microtopographic Features," Optical Engineering, vol. 18, No. 2, 1979, pp. 125-136.

* cited by examiner

*Primary Examiner* — Tara S Pajoohi Gomez
(74) *Attorney, Agent, or Firm* — Ann Marie Mewherter (57) ABSTRACT

Systems and methods for inspecting a specimen are provided. One system includes an illumination subsystem configured to direct light to the specimen at an oblique angle of incidence. The light is polarized in a plane that is substantially parallel to the plane of incidence. The system also includes a detection subsystem configured to detect light scattered from the specimen. The detected light is polarized in a plane that is substantially parallel to the plane of scattering. In addition, the system includes a processor configured to detect defects on the specimen using signals generated by the detection subsystem. In one embodiment, such a system may be configured to detect defects having a size that is less than half of a wavelength of the light directed to the specimen.

23 Claims, 8 Drawing Sheets

SYSTEMS AND METHODS FOR INSPECTING SPECIMENS INCLUDING SPECIMENS THAT HAVE A SUBSTANTIALLY ROUGH UPPERMOST LAYER

BACKGROUND OF THE INVENTION

1. Field of the Invention

The present invention generally relates to systems and methods for inspecting a specimen. Certain embodiments relate to systems and methods for inspecting a specimen that includes a substantially rough uppermost layer.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various times during a semiconductor manufacturing process to detect defects on wafers. Inspection has always been an important part of fabricating semiconductor devices such as integrated circuits. However, as the dimensions of semiconductor devices decrease, inspection becomes even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Many different types of inspection systems have been developed for the inspection of wafers. One example of an inspection system that is configured to inspect relatively smooth surfaces such as those of bare silicon wafers uses oblique illumination with a polarization combination called "P-U," which indicates that the incident light is P-polarized (i.e., polarized in the plane of incidence) and the scattered light that is detected is unpolarized (i.e., light having all polarizations is collected and detected). The sensitivity of such a system is greatest for inspection of substantially smooth surfaces. However, relatively rough surfaces scatter a substantial amount of light in the P-U configuration. In this manner, scattering from relatively small defects can be much lower than the surface scattering. As such, the signal-to-noise ratio of the inspection data may not be high enough to allow accurate detection of relatively small defects.

In another example of a wafer inspection system, a "double-dark field" configuration can be used for inspecting relatively rough surfaces for contamination and other defects. In particular, using S-polarized (i.e., polarized perpendicular to the plane of incidence) obliquely incident light results in a dark fringe at the surface, which produces substantially little light scattered from the surface itself. Such illumination used with an analyzer oriented perpendicular to the plane of scatter and an aperture limited to "side-angle collection" can reduce the contribution of unwanted surface scattering to the background noise by several orders of magnitude. Large particles and defects located on the surface of the wafer can be detected relatively easily using this configuration since they do not experience the dark fringe effect and therefore perturb (or scatter) the incident electric field efficiently compared to the surface.

Side-angle collection typically involves limiting the collected scattered light to azimuthal angles reasonably close to +/−90 degrees with respect to the plane of incidence. For example, in the SP1-TBI system that is commercially available from KLA-Tencor Corporation, San Jose, Calif., there are two configuration for side-angle collection: one that collects light within 10 degrees of +/−90 degrees (i.e., a 20 degree azimuthal width on each side of the plane of incidence), and one that collects light within 20 degrees of +/−90 degrees (i.e., 40 degrees of azimuthal width on each side of the plane of incidence).

The S-S polarization combination with side-angle collection configuration works well for particles having a size greater than approximately one-half the wavelength of the incident light. Such defect detection capability is achievable due, at least in part, to the fact that the S-S side-angle configuration is substantially effective at reducing the scattering from the surface. Unfortunately, this configuration is also substantially effective at reducing the scattering from small defects, which are generally defined herein as defects having a size that is smaller than one-half the wavelength of the incident light. However, once the defect size increases to approximately one-half the wavelength of the light or greater, a typical defect begins to scatter significantly into the side-angle collection space. Since the surface scattering is suppressed, this configuration provides a significant signal-to-noise advantage for the inspection system for the detection of relatively large defects on relatively rough surfaces.

Between about 1993 and about 1998, semiconductor processes using material that have rough surfaces were subject to failure caused by defects having a size of approximately 200 nm and larger. Therefore, the desired defect detection capability could be achieved by using an illumination wavelength of 488 nm, which Surfscan instruments that are commercially available from KLA-Tencor, used at the time. But Moore's law marches on, and today customers are expressing the need to detect defects having a size of 150 nm, 100 nm, or even smaller, on wafers having even relatively rough surfaces. Therefore, even an ultraviolet (UV) wavelength of, say, 355 nm combined with the S-S side-angle technique is not sufficient for detecting defects of such sizes on wafers having a relatively rough upper surface.

Accordingly, it may be advantageous to develop systems and methods for inspecting a specimen, particularly a specimen having a relatively rough uppermost layer, that are capable of detecting defects having sizes that are less than about half of the incident wavelength used for inspection with relatively high accuracy.

SUMMARY OF THE INVENTION

The following description of various embodiments of systems and methods for inspecting a specimen is not to be construed in any way as limiting the subject matter of the appended claims.

One embodiment relates to a system configured to inspect a specimen. The system includes an illumination subsystem that is configured to direct light to the specimen at an oblique angle of incidence. The light is polarized in a plane that is substantially parallel to the plane of incidence. The system also includes a detection subsystem that is configured to detect light scattered from the specimen. The detected light is polarized in a plane that is substantially parallel to the plane of scattering. In addition, the system includes a processor that is configured to detect defects on the specimen using signals generated by the detection subsystem.

In one embodiment, the detection subsystem is configured to detect the light scattered in only a portion of a collection space of the detection subsystem. In one such embodiment, a level of the light scattered in the portion is lower than a level of the light scattered in another portion of the collection space. In another such embodiment, the portion of the collection space includes a portion of two forwarding scattering quadrants. In an additional embodiment, the detection subsystem is configured such that at least a substantial portion of the detected light includes light that is not scattered by a surface of the specimen.

In some embodiments, the detection subsystem includes an aperture that is configured to block the light scattered in a portion of a collection space of the detection subsystem. In one such embodiment, the system is configured to move the aperture into or out of an optical path of the detection subsystem based on characteristics of the specimen. In another such embodiment, the aperture is selected based on characteristics of the specimen. In a further such embodiment, characteristics of the aperture are determined based on measurements of light scattered from the specimen across substantially an entirety of the collection space. In an additional embodiment, the detection subsystem includes a polarizing component having a pass axis that is different for different scattering azimuthal angles.

In one embodiment, the specimen includes an uppermost layer having substantial roughness. In another embodiment, the defects include defects having a size from about 100 nm to about 200 nm. Each of the embodiments of the system described above may be further configured as described herein.

Another embodiment relates to a system that is configured to inspect a specimen. This system includes an illumination subsystem that is configured to direct light to the specimen at an oblique angle of incidence. The light is polarized in a plane that is substantially parallel to the plane of incidence. The system also includes a detection subsystem that is configured to detect light scattered from the specimen. The detected light is polarized in a plane that is substantially parallel to the plane of scattering. In addition, the system includes a processor that is configured to detect defects on the specimen using signals generated by the detection subsystem. A size of the defects is less than half of a wavelength of the light directed to the specimen. This system may also be further configured as described herein.

An additional embodiment relates to a method for inspecting a specimen. The method includes directing light to the specimen at an oblique angle of incidence. The light is polarized in a plane that is substantially parallel to the plane of incidence. The method also includes detecting light scattered from the specimen. The detected light is polarized in a plane that is substantially parallel to the plane of scattering. In addition, the method includes detecting defects on the specimen using signals responsive to the detected light.

In one embodiment, the detected light includes the light scattered in only a portion of a collection space containing the plane of scattering. In one such embodiment, a level of the light scattered in the portion is lower than a level of the light scattered in another portion of the collection space. In another such embodiment, the portion includes a portion of two forward scattering quadrants. In some embodiments, at least a substantial portion of the detected light includes light that is not scattered by a surface of the specimen.

In another embodiment, the method includes blocking the light scattered in a portion of a collection space containing the plane of scattering. In some embodiments, the method includes blocking the light as described above using an aperture and moving the aperture into or out of a path of light collected in the collection space based on characteristics of the specimen. In an additional embodiment, the method includes blocking the light as described above and selecting the portion of the collection space based on characteristics of the specimen. In a further embodiment, the method includes measuring light scattered from the specimen across substantially an entire collection space containing the plane of scattering, determining characteristics of an aperture based on results of the measuring step, and blocking the light scattered in a portion of the entire collection space using the aperture.

In one embodiment, the specimen includes an uppermost layer having substantial roughness. In another embodiment, the defects include defects having a size from about 100 nm to about 200 nm. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or any other specimen on which defects of interest may be located. Although the terms "specimen" and "wafer" are used interchangeably herein, it is to be understood that embodiments described herein with respect to a wafer may configured and/or used for any other specimen as described above.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, and a conductive material. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
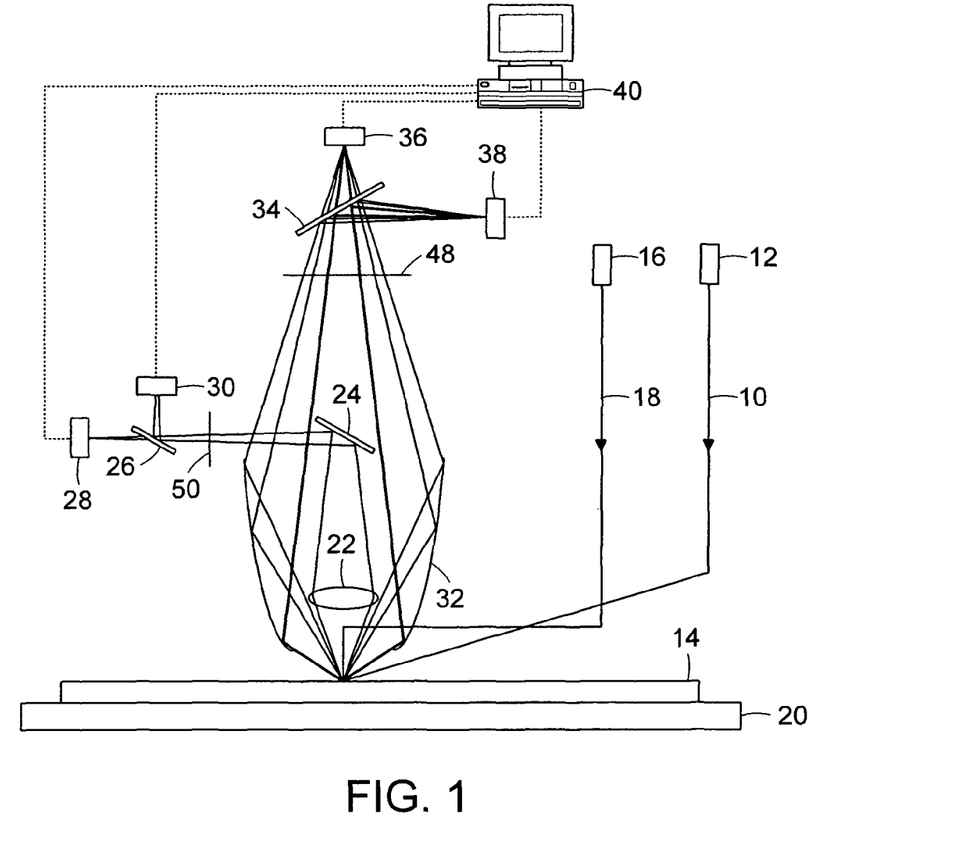
FIG. 1 is a schematic diagram illustrating a cross-sectional view of one embodiment of a system that is configured to inspect a specimen.

One embodiment of a system that is configured to inspect a specimen is illustrated in FIG. 1. The system shown in FIG. 1 is configured for unpatterned wafer inspection and is based on the SP1-TBI system, which is commercially available from KLA-Tencor, San Jose, Calif. This inspection system is described in more detail in U.S. Pat. No. 6,538,730 to Vaez-Iravani et al., which is incorporated by reference as if fully set forth herein. The system shown in FIG. 1 may be further configured as described in this patent for patterned and unpatterned wafer inspection. For the sake of clarity, some of the components and details of the system have been omitted from FIG. 1 and the corresponding description presented herein. In addition, U.S. Pat. No. 6,538,730 is related to U.S. Pat. Nos. 6,201,601 to Vaez-Iravani et al. and 6,271,916 to Marxer et al., which are also incorporated by reference as if fully set forth herein. The system shown in FIG. 1 may be further configured as described in these patents.

The system shown in FIG. 1 includes an illumination subsystem. The illumination subsystem may be configured to generate light 10. For instance, the illumination subsystem may include light source 12, which is configured to generate light 10. The illumination subsystem is configured to direct light 10 to wafer 14 at an oblique angle of incidence. The illumination subsystem may include a number of optical components (not shown) positioned in a path of light 10 such as folding mirror(s), beam splitter(s), polarizing component (s), filter(s), and lenses. The angle of incidence may vary depending on, for example, the characteristics of the light and the characteristics of the specimen. One suitable angle of incidence may be about 70° from normal to the upper surface of the wafer.

The illumination subsystem also includes light source 16. Light source 16 is configured to generate light 18, which is directed by the illumination subsystem to wafer 14 at a substantially normal angle of incidence. The illumination subsystem may include a number of optical components (not shown) positioned in the path of light 18. These optical components may include any of those described above.

Light sources 12 and 16 may include any suitable light sources known in the art such as lasers. In a different embodiment, the system may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art. In any of the above embodiments, light 10 may have one or more characteristics such as wavelength and/or polarization that are different than the characteristics of light 18. Alternatively, light 10 may have substantially the same characteristics as light 18.

Wafer 14 is supported on stage 20, which may be rotated and translated such that light 10 and 18 illuminates an area or spot on the wafer that moves in a spiral path. Alternatively, light 10 and 18 may be scanned over the wafer in any manner known to those skilled in the art to trace the spiral path or another type of scan path across the wafer.

Illumination of the wafer will cause scattering of the light from the wafer. In addition, both oblique incidence light and normal incidence light may be scattered from the wafer. The system shown in FIG. 1 includes a detection subsystem that is configured to collect light scattered from the specimen and to generate signals responsive to the scattered light. The signals can be used to detect defects on the specimen as described further herein.

The detection subsystem includes lens collector 22, mirror 24, beam splitter 26, and detectors 28 and 30, which form a "narrow" channel of the detection subsystem. In other words, light scattered from the illuminated area on the wafer along directions relatively close to normal to the surface of the wafer is collected and focused by lens collector 22. In this manner, lens collector 22 collects light scattered from the wafer at relatively "narrow" scattering angles. Lens collector 22 directs the collected light to mirror 24, which directs the light to beam splitter 26. Beam splitter 26 is configured to direct one portion of the light to detector 28 and the other portion of the light to detector 30. One detector may be used to detect light scattered at relatively narrow angles due to illumination by the normal incidence beam, and the other detector may be used to detect light scattered at relatively narrow angles due to illumination by the oblique incidence beam. Detectors 28 and 30 may include any suitable detectors known in the art (e.g., photomultiplier tubes (PMTs)). In addition, detectors 28 and 30 may be similarly or differently configured. The narrow channel portion of the detection subsystem may include any other optical components (not shown) known in the art. For example, one or more polarizing components may be placed in the path of the collected light. In addition, a spatial filter may be included in the narrow channel portion of the detection subsystem to prevent the specular reflection of the normal incidence beam from reaching detectors 28 and 30.

The detection subsystem also includes ellipsoidal mirror 32, beam splitter 34, and detectors 36 and 38, which form a "wide channel" of the detection subsystem. In other words, light scattered from the illuminated area on the wafer along directions relatively far from normal to the surface of the wafer is collected and focused by ellipsoidal mirror 32. In this manner, ellipsoidal mirror 32 collects light scattered from the wafer at relatively "wide" scattering angles. Ellipsoidal mirror 32 directs the collected light to beam splitter 34. Beam splitter 34 is configured to direct one portion of the light to detector 36 and the other portion of the light to detector 38. One detector may be used to detect light scattered at relatively wide angles due to illumination by the normal incidence beam, and the other detector may be used to detect light scattered at relatively wide angles due to illumination by the oblique incidence beam. Detectors 36 and 38 may include any suitable detectors known in the art (e.g., PMTs). In addition, detectors 36 and 38 may be similarly or differently configured. The wide channel portion of the detection subsystem may include any other optical components (not shown) known in the art. For example, one or more polarizing components may be placed in the path of the collected light.

Detectors 28, 30, 36, and 38 are configured to generate signals responsive to the scattered light. Processor 40 is coupled to detectors 28, 30, 36, and 38 by transmission media as shown by the dotted lines in FIG. 1. The transmission media may include any suitable transmission media known in the art. In addition, one or more additional components (not shown) may be interposed between the detectors and the processor such as analog-to-digital converters. In this manner, signals generated by the detectors can be sent to the processor. The processor may be configured to use the signals to detect defects on the wafer. The processor may also be configured to use any algorithm or method known in the art for detecting the defects using the signals. In addition, the processor may include any suitable processing component known in the art.

As described further herein, increased sensitivity to relatively small defects on relatively rough surfaces is provided by a dark field scanning surface inspection system such as the system described above with modifications described herein. Small defects are generally defined herein as defects having a size (e.g., a polystyrene latex (PSL) sphere equivalent size) of less than about half of the wavelength of the incident light used for inspection. More specifically, defects such as particles having a size in a range from about 100 nm to about 200 nm can be detected on relatively rough films used in semiconductor wafer processing such as polysilicon, aluminum, copper, tungsten, and other similarly rough materials using the system and method embodiments described herein.

The systems and methods described herein utilize a different polarization combination (i.e., the polarization of the incident light in combination with the polarization of the detected light) than those previously used in inspection systems with a relatively large solid angle collection space. The basic problem for most polarization combinations is that solid angles at which the surface scattering is suppressed are also the very same solid angles at which relatively small defect scattering is suppressed. Thus, most polarization combinations cannot be used for small defect detection.

Figure 2:
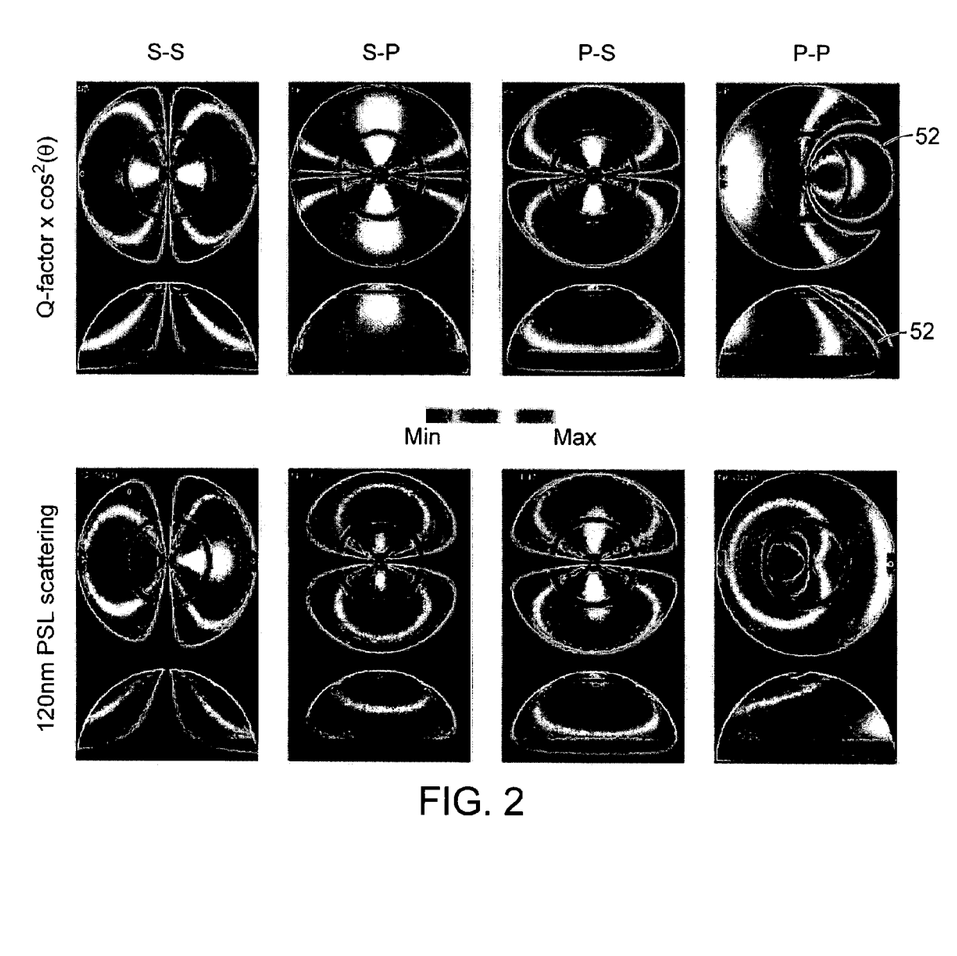
FIG. 2 includes plots illustrating simulated surface and small defect scattering patterns for various combinations of incident polarization and detection polarization.

Such defect detection problems are evident in the surface and small defect scattering patterns shown in FIG. 2, which were simulated for S-S, S-P, P-S, and P-P polarization combinations. These scattering patterns were generated using the decades-old theoretical description of rough-surface scattering developed by S. O. Rice. In general, using first-order vector perturbation theory, Rice derived the expected scattering from a surface as a function of input and output polarization, wavelength, refractive index, and power spectral density. This theoretical description is known in the art and thus, for the sake of brevity, will not be described further herein. However, additional description of the rough-surface scattering theory developed by S. O. Rice can be found in Rice, S. O., "Reflection of electromagnetic waves from slightly rough surfaces," *Communications in Pure and Applied Mathematics*, vol. 4, p. 351, 1951, and Church, E. L., Sanger, G. M., and Takacs, P. Z. "Relationship between surface scattering and microtopographic features," *Optical Engineering*, vol. 19, no. 2, pp. 125-136, 1979, which are incorporated by reference as if fully set forth herein.

The top row of scattering patterns shown in FIG. 2 are surface scattering patterns, and the bottom row includes small defect (e.g., 120 nm PSL sphere) scattering patterns. Each plot shown in FIG. 2 includes a top view and a side view of the collection space, which in this example is a scattering hemisphere. Incident light is from the left of the plots at an oblique angle of incidence of 70 degrees from normal to an upper surface of the specimen. All of the plots are independently and arbitrarily scaled. Dark regions in the plots indicate regions of the collection space in which levels of scattering are relatively low. Light regions in the plots indicate regions of the collection space in which levels of scattering are relatively high. The dark circular regions within the scattering hemisphere are used to indicate regions of the collection space in which the system shown in FIG. 1 does not collect light.

Comparing the upper and lower scattering patterns in each column (i.e., the surface and small defect scattering patterns for each polarization combination) reveals that the basic patterns, and in particular the regions in which the scattering is at a minimum, are approximately the same for three of the four polarization combinations. The one exception is the P-P polarization combination. In the scattering patterns generated for P-P polarization, there is a localized region in the collection space in which surface scattering is relatively low and defect scattering is reasonably high. These characteristics of the P-P polarization scattering patterns provide an opportunity to improve the sensitivity of inspection systems to relatively small defects. Using a P-P polarization combination for relatively small defect detection is counter-intuitive and non-obvious for two reasons: first, P-polarization tends to maximize the electric field at the surface of the specimen; and second, defects several times smaller than the incident wavelength generally scatter substantially little light and detection of these defects benefits from as large a collection aperture as possible.

In one embodiment, however, a system configured to inspect a specimen includes an illumination subsystem configured to direct light to the specimen at an oblique angle of incidence. The light is polarized in a plane that is substantially parallel to the plane of incidence (i.e., substantially P-polarized). This illumination subsystem may be configured as shown in FIG. 1. For example, the illumination subsystem includes light source 12, which, in one embodiment, may be configured to generate substantially P-polarized light that is directed to the specimen at an oblique angle of incidence. Alternatively, the illumination subsystem may include a polarizing component (not shown) positioned in the optical path of oblique incidence beam 10. The polarizing component may be configured to alter the polarization of the light generated by light source 12 such that the light directed to the specimen is substantially P-polarized. The polarizing component may, alternatively, be configured to filter non-P-polarized light from the light that is directed to the specimen. The polarizing component may include, for example, a linear polarizer or any other suitable polarizing component known in the art.

This embodiment of the system also includes a detection subsystem that is configured to detect light scattered from the specimen. The detected light is polarized in a plane that is substantially parallel to the plane of scattering (i.e., substantially P-polarized). This detection subsystem may be configured as shown in FIG. 1 with appropriate modifications described herein. For example, a simple linear polarizer (not shown) could be positioned in an optical path of the detection subsystem. A linear P-polarizing component is currently used in the system shown in FIG. 1 and is positioned above the collector. However, a linear polarizer is generally not sufficient for the detection of defects described herein.

Instead, the detection subsystem preferably includes a polarizing component that has a pass axis that is different for different scattering azimuthal angles across the polarizing component. In this manner, the polarizing component may have a pass axis that is in the plane of the scattered light vector at all positions in the collection aperture. Such a polarizing component may be particularly suitable for use in the systems described herein for a number of reasons. For example, this polarizing component will reduce the signal-to-noise degradation that may occur due to the interaction of light with a polarizing component. In this manner, a P-polarizer/analyzer having a pass axis that varies continuously with scattering azimuth may be used to increase the sensitivity of the system in comparison to the sensitivity that can be achieved using a linear polarizer, which is typically used in the collection optics of systems such as that shown in FIG. 1. Therefore, the polarizing component currently used in the system shown in FIG. 1 may be replaced with a polarizing component that yields substantially P-polarized light for all scattering angles.

Such "matching" of the pass axis and the plane of the scattered light vector may be particularly important for scattering angles in the forward and near-forward directions since light scattered from defects on a wafer may be located in these areas of the collection space while light scattering from the surface of the wafer tends to be relatively low in these areas. In one such embodiment, if the light scattered in only a portion of the collection space is used for defect detection as described further herein, the embodiments of the polarizing components described herein may be configured to alter the polarization of the light in only the portion of the collection space. For example, the polarizing component may include only a portion of the polarizing component embodiments described herein.

Figure 3:
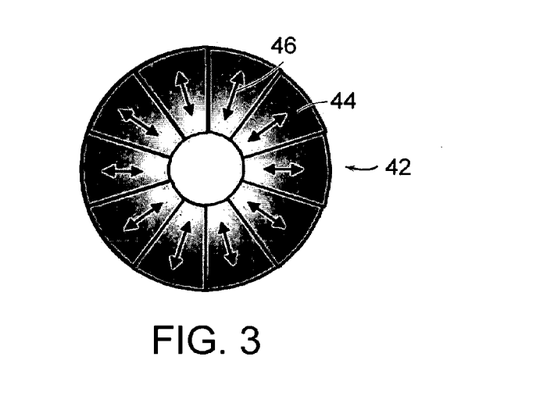
FIG. 3 is a schematic diagram illustrating a cross-sectional view of one embodiment of a polarizing component that includes a number of segments having different pass axis orientations.

If a polarizer whose pass axis varies continuously with angle cannot be manufactured, as may be the case, a segmented polarizer may be included in the detection subsystem. One embodiment of such a polarizing component is illustrated in FIG. 3. As shown in FIG. 3, polarizing component 42 is a segmented polarizer that is formed of multiple sections 44 of linear polarizers butted against each other, each having a different orientation for pass axis 46. As further shown in FIG. 3, the segmented polarizer may include tens segments, each including a linear polarizer having a differently oriented pass axis. However, it is to be understood that the number of polarizer segments including in polarizing component 42 may vary depending on, for example, the amount of background scattering expected from a specimen and the desired level of background scattering suppression. For instance, as the number of segments in the polarizing component increases, the background scatter suppression may also improve thereby better approximating the ideal case of background scatter (e.g., the background scatter that can be obtained using a polarizer having a continuously varying pass axis), which is illustrated in FIG. 4.

Figure 4:
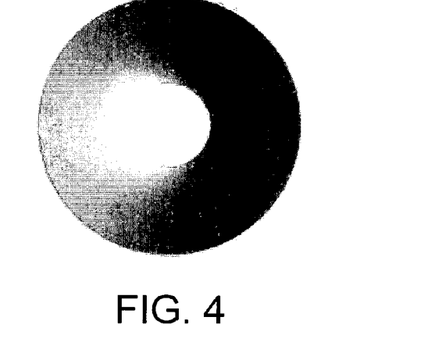
FIG. 4 is a plot illustrating a surface scattering pattern simulated for light scattered from the surface and passed through a polarizing component having a pass axis orientation that varies continuously with scattering angle.
Figure 5:
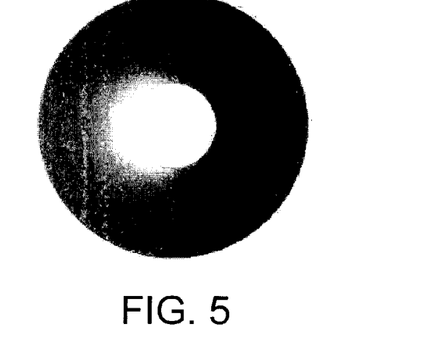
FIG. 5 is a plot illustrating a surface scattering pattern simulated for light scattered from the surface and passed through the polarizing component shown in FIG. 3.

In particular, FIG. 4 illustrates the Rice Q-factor simulated for P-polarized illumination and a polarizing component whose pass axis is in the plane of the scattered light vector at all positions in the collection aperture. In this manner, the surface scattering pattern illustrated in FIG. 4 simulates the pattern of light scattered from a specimen after passing through a polarizer that has an infinite number of segments. For the sake of comparison, FIG. 5 illustrates the Rice Q-factor simulated for P-polarized illumination and a polarizing component having ten segments positioned in the collection aperture. This polarizer may be configured as shown in FIG. 3. Comparison of the surface scattering patterns illustrated in FIGS. 4 and 5 indicates that using a segmented polarizer having ten segments as shown in FIG. 3 produces a surface scattering pattern that is a reasonable approximation of the ideal surface scattering pattern. In this manner, a segmented P-polarizer/analyzer may provide a reasonable approximation of a polarizer having a pass axis that varies continuously with scattering azimuth. Therefore, a segmented polarizer may be used to substantially improve the sensitivity of the system, particularly in comparison to the sensitivity that can be achieved using the linear polarizers typically used in the collection optics of systems such as that shown in FIG. 1.

A polarizing component configured as described above may be positioned in collection aperture 48 of the detection subsystem, as shown in FIG. 1. The position of the collection aperture may vary depending on, for example, the optical configuration of the system. In addition, as shown in FIG. 1, the polarizing component may be positioned in the path of the light collected by ellipsoidal mirror 32, which collects light scattered at relatively wide angles as described above. The polarizing component may be located in the path of this light since this light may be more sensitive to relatively small defects than light scattered at relatively narrow angles, which is collected by lens collector 22. However, if the light scattered at relatively narrow angles is also sufficiently sensitive to relatively small defects, then signals generated by detectors 28 and 30 may also be used for relatively small defect detection. In such an embodiment, a polarizing component as described above may also or alternatively be positioned in collection aperture 50 of the detection subsystem, as shown in FIG. 1. The position of collection aperture 50 may also vary as described above.

In some embodiments, the detection subsystem may be configured to detect the light scattered in only a portion of a collection space of the detection subsystem. In one such embodiment, a level of the light scattered in the portion is lower than a level of the light scattered in another portion of the collection space. In other words, the light scattered from the surface of a specimen that includes an uppermost layer having substantial roughness may scatter a relatively large amount of light in certain portions of the collection space. In other portions of the collection space, the surface scattering may be relatively small while scattering from defects including relatively small defects may be sufficient for defect detection. Therefore, the detection subsystem is preferably configured to detect light scattered in portions of the collection space in which light scattered from the surface of the specimen is relatively low and light scattered from defects is reasonably high.

In another such embodiment, the portion of the collection space in which light is detected may include a portion of two forward scattering quadrants. However, the portion of the collection space in which scattered light is detected may vary depending on the directions in which defects on the specimen scatter light. In this manner, the portion of the collection space may vary depending on characteristics of the defects that are to be detected. As such, the detection subsystem may be configured such that at least a substantial portion of the detected light includes light that is not scattered by a surface of the specimen. Instead, a substantial portion of the detected light includes light scattered from defects on the surface of the specimen thereby increasing defect sensitivity of the system.

Since many inspection systems such as the system shown in FIG. 1 include detection subsystems that can collect light in a relatively large collection space, these detection subsystems may be altered such that the detection subsystem does not detect light scattered in the entire collection space. In one such embodiment, the detection subsystem includes an aperture that is configured to block the light scattered in a portion of the collection space of the detection subsystem. As such, the aperture may be used to select which portions of the collection space are used for inspection. The aperture is preferably configured to block undesired light (e.g., light scattered from the surface of the specimen) and to pass light corresponding to the minimum or near-minimum in surface scattering for the P-P polarization combination. This near-minimum corresponds approximately to dark regions 52 in the scattering patterns for P-P polarization shown in FIG. 2. In this manner, portions of the collection space in which surface scattering is significant are blocked by the aperture, and regions in which surface scattering is small are passed by the aperture.

Figure 6:
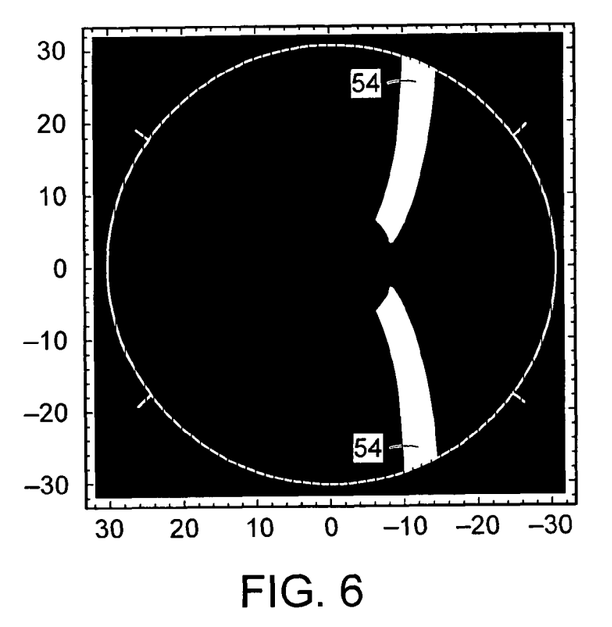
FIGS. 6-7 are schematic diagrams illustrating a cross-sectional view of different embodiments of an aperture that may be positioned in an optical path of a detection subsystem included in the system embodiments described herein.
Figure 7:
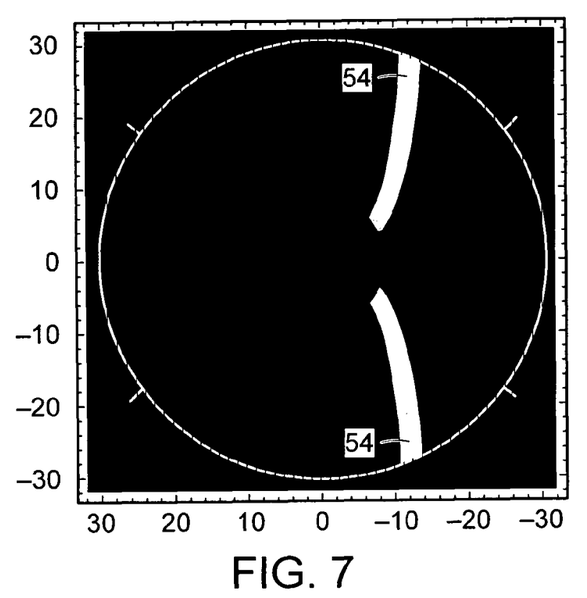

Two different embodiments of an aperture that may be included in the detection subsystem are shown in FIGS. 6 and 7. The shape of these apertures appears substantially different than dark regions 52 shown in FIG. 2 since the collectors shown in FIG. 1 transform the polar scattering angles. In addition, the location of the aperture in the detection subsystem contributes to the unusual looking shapes. The apertures shown in FIGS. 6 and 7 may be positioned at collection aperture 48 and/or collection aperture 50 shown in FIG. 1 depending on which collector(s) are used for defect detection. In some embodiments, a polarizing component as described above and a blocking aperture as described herein may both be positioned approximately at the collection aperture. The arrangement of the polarizing component with respect to the blocking aperture will not affect the performance of the systems described herein. In other words, the collected light may pass through the polarizing component and then through the blocking aperture or vice versa.

As shown in FIGS. 6 and 7, both of the apertures include two openings 54 through which light scattered from the specimen can pass. Light in all other portions of the collection space will be substantially blocked by the apertures. In addition, as shown in FIGS. 6 and 7, the openings in the apertures have relatively small solid angles. As further shown in FIGS. 6 and 7, the solid angles of the openings may vary somewhat. In particular, the geometry of the aperture may be determined based on appropriate analysis using, for example, the Rice equations. In this manner, the portions of the scattering space, or hemisphere in some systems, in which scattered light is detected and used for defect detection may be determined theoretically by the Rice rough surface scatter equations. In general, the solid angles of the openings are preferably large enough to allow enough light scattered from defects on the specimen to pass through to the detector while blocking enough of the light scattered from the surface of the specimen such that this scattered light does not interfere with defect detection.

It is to be understood that the apertures shown in FIGS. 6 and 7 are presented merely as examples of possible apertures. Apertures having many other geometries may also be used in the detection subsystem. An appropriate geometry for the aperture will depend on, for example, the configuration of the system, the characteristics of light scattered from the surface of the specimen, and the characteristics of the light scattered from defects on the specimen. Furthermore, the apertures described herein are relatively straightforward to construct. For example, the apertures can be constructed using manufacturing techniques similar to those used to construct the "butterfly" side-angle collection apertures that are currently used in inspection systems such as that illustrated in FIG. 1.

As described above, the configuration of the aperture(s) used in the detection subsystem may be selected based on characteristics of the specimen. In addition, an appropriate configuration may be determined based on characteristics of the specimen and characteristics of the inspection system using the Rice equations. Since the Rice equations are a first-order approximation and assume an ideal surface, it is possible that the scattering patterns of some surfaces or films may deviate somewhat from those shown in FIG. 2. In this case, the apertures shown in FIGS. 6 and 7 may not be ideal for some types of specimens and/or some types of inspection systems.

In one embodiment, therefore, the characteristics of the aperture may be determined based on measurements of light scattered from a specimen across substantially an entirety of the collection space. In this manner, improved sensitivity of the system may be achieved using empirical measurements of the scattering pattern of one or more wafers of a process level of interest, at an appropriate plane within the collection optics. For example, by imaging the collection aperture plane with a detector such as a charge coupled device (CCD) camera or any other suitable detector known in the art, it is possible to determine the exact scattering pattern of a rough film of interest. A negative image of this scattering pattern can be transferred to an aperture configuration, which can be manufactured and placed at the same plane in the detection subsystem. In this manner, a "custom" aperture may be designed and constructed to eliminate the maximum amount of surface scatter. In addition, the wafer-to-wafer and/or process-to-process variation in the scattering patterns may be measured and characterized to even more effectively determine characteristics of an appropriate "custom" aperture.

Figure 8:
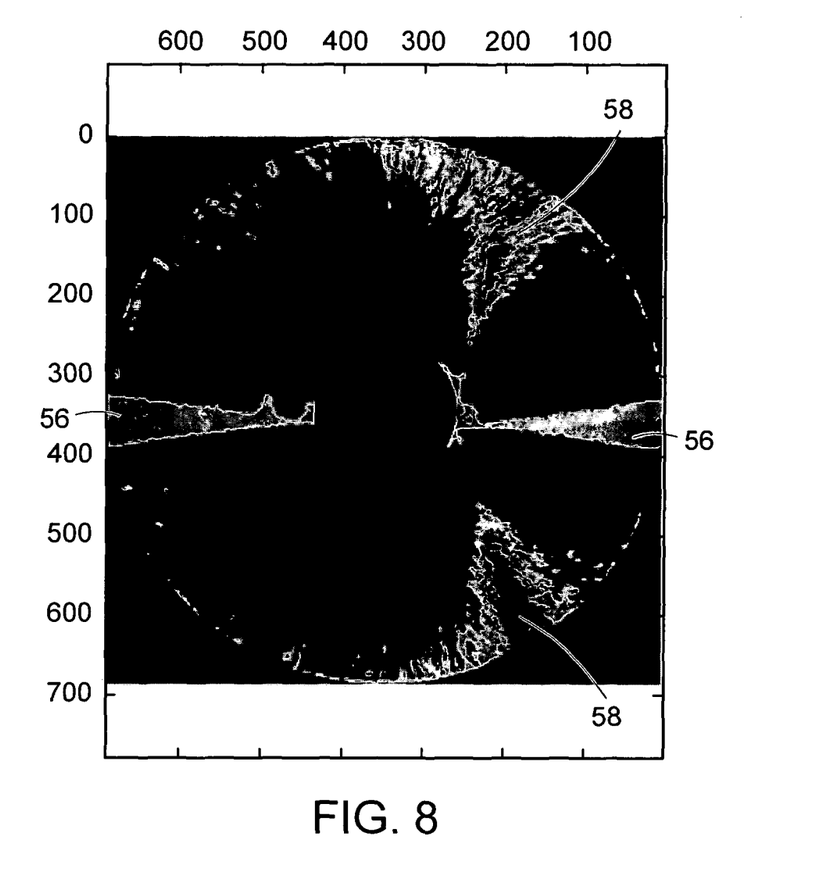
FIG. 8 is a plot illustrating a scattering pattern from a rough film surface measured in the aperture plane of the SP1-DLS system modified to include a P-P polarization combination.

One example of a scattering pattern of a rough film that does not exactly match the expected scattering pattern based on the simple scatter theory is shown in FIG. 8. The scattering pattern shown in FIG. 8 was observed in the aperture plane of the SP1-DLS system using the P-P polarization combination described herein. As shown in FIG. 8, regions 56, which are approximately horizontal, indicate portions of the collection space in which the scatter has been purposely blocked to prevent specular beam effects. Regions 58, which are oriented in a more vertical direction than regions 56, indicate portions of the collection space in which surface scattering is minimal. These regions are similar, but not identical, to the pass regions of the apertures shown in FIGS. 6 and 7. Therefore, inspection of this particular rough film surface may benefit from using a "custom" aperture in the detection subsystem.

In some embodiments, therefore, the system may include a number of different apertures. Each of the different apertures may be designed for use during inspection of different types of wafers and/or wafers fabricated using different types of processes. In this manner, the aperture that is used for an inspection process may be selected based on characteristics of the specimen. In addition, the system may be configured to change the aperture positioned in the optical path of the detection subsystem based on the inspection process that is being performed thereby effectively changing the aperture based on the characteristics of the specimen.

The systems described herein are particularly useful for inspection of specimens that include an uppermost layer having substantial roughness, but the systems may also be used for inspection of specimens that have relatively smooth surfaces. In this manner, even if the system includes only one aperture, the system may be configured to move the aperture into or out of the optical path of the detection subsystem based on the characteristics of the specimen. For instance, if a specimen having a relatively rough surface is to be inspected, the system may move the aperture into the optical path of the detection subsystem. Alternatively, if a specimen having a relatively smooth surface is to be inspected, the system may move the aperture out of the optical path of the detection subsystem. In this manner, the systems described herein may include a removable aperture that allows all other features of the inspection system, some of which are described in the patents incorporated by reference above, to be maintained without impact. The system may be configured to use any device (not shown) known in the art that can be coupled to the aperture(s) and that can be controlled (e.g., by processor 40) to alter a position of the aperture(s). Some apertures, however, may not substantially reduce the sensitivity of the system for inspection of relatively smooth surfaces. In this manner, the aperture may be positioned in the optical path of the detection subsystem regardless of the characteristics of the specimen being inspected.

Figure 9:
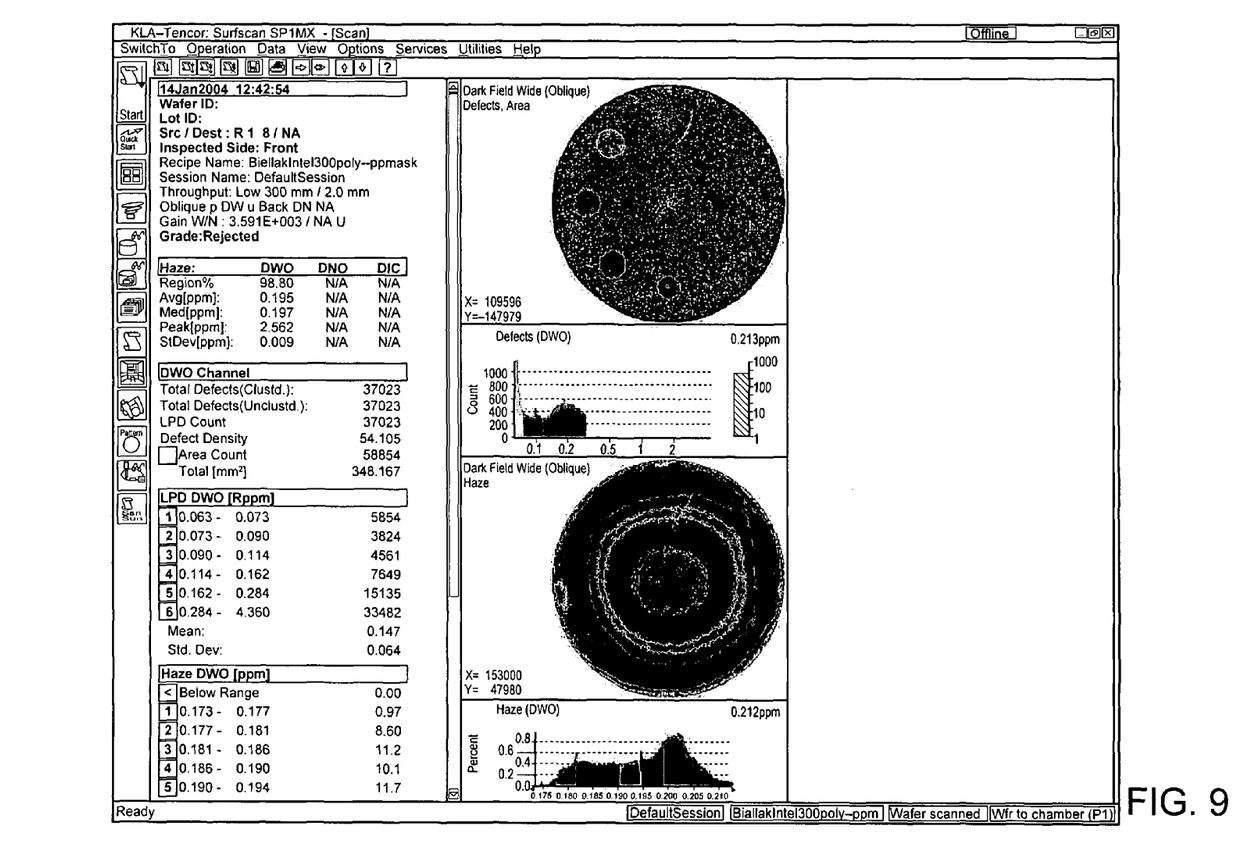
FIG. 9 is a user interface illustrating data generated by inspecting a specimen having a rough film surface using the SP1-DLS system modified to have a P-P polarization combination and an aperture positioned in a path of scattered light collected from the specimen.

FIG. 9 is a user interface that illustrates results of inspection of a rough polysilicon film formed on a wafer that was performed using the Surfscan SP1-DLS platform. The SP1-DLS platform was modified as described herein to have a P-P polarization combination and an aperture configured as described above. PSL spheres of a variety of sizes were deposited on the polysilicon film. As shown in FIG. 9, the system modified to include the P-P combination and a "P to P forward scatter" aperture described above detected 155 nm PSL spheres with an acceptable signal-to-noise ratio. Using the P-P polarization combination with the collection aperture and the ten segment P-analyzer shown in FIG. 3, 126 nm PSL spheres were easily detected. In this manner, the system embodiments described herein can be used to detect defects on a specimen having a size from about 100 nm to about 200 nm. In another embodiment, the size of the defects detected by the system embodiments described herein is less than half of the wavelength of the light directed to the specimen.

Figure 10:
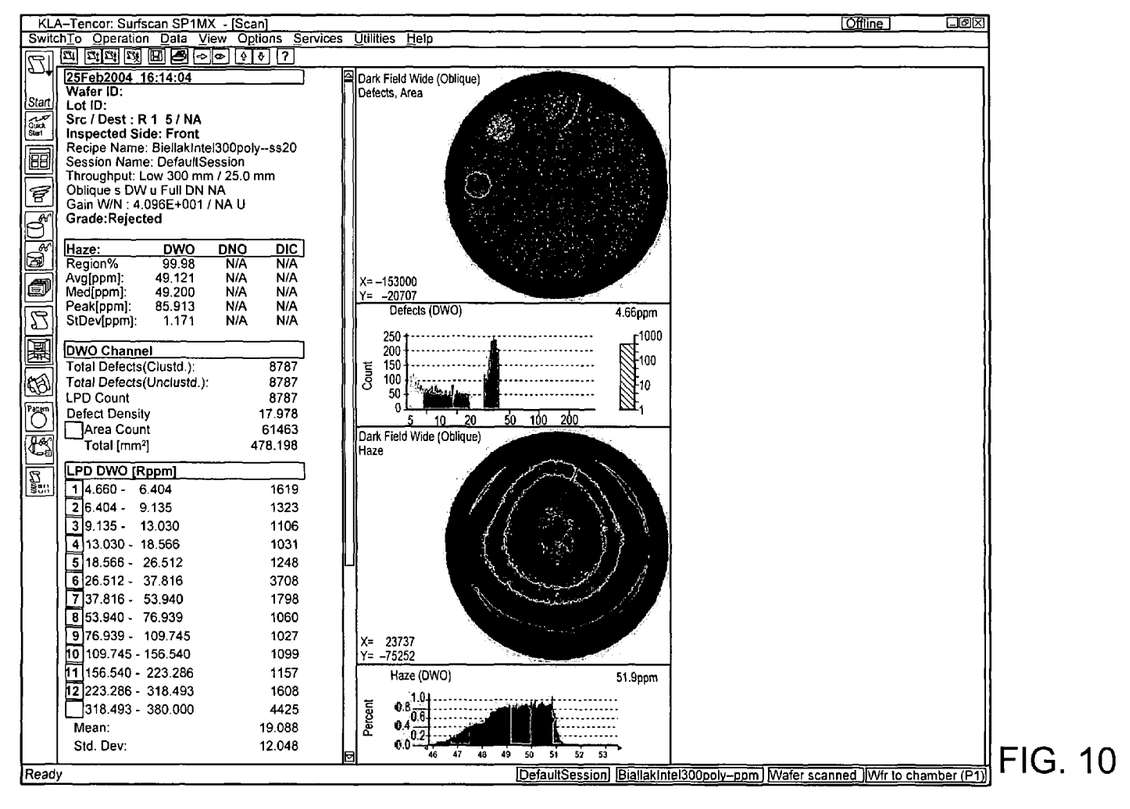
FIG. 10 is a user interface illustrating data generated by inspecting a specimen having a rough film surface using the SP1-DLS system configured to have a S-U polarization combination and detection across substantially the entire collection space of the system.

FIG. 10 is a user interface that illustrates results of inspection of the rough polysilicon film that was performed using the Surfscan SP1-DLS platform without the improvements described herein. In other words, this inspection data was generated using an S-U polarization combination with detection of the light collected across the entire collection aperture of the system. In this manner, the collection aperture described above was not positioned in the optical path of the detection subsystem during this inspection. This inspection configuration was previously considered to be the best configuration for this system. Larger particles detected by this inspection were removed from the inspection data for clarity. As shown in FIG. 10, this inspection configuration was not able to detect as many 155 nm PSL spheres or as many 126 nm PSL spheres as the inspection configuration used to generate the inspection data shown in FIG. 9. Therefore, comparison of the inspection data shown in FIGS. 9 and 10 illustrates that the modified embodiments of the system configurations described herein are much more sensitive to relatively small defects than other system configurations.

Although the system embodiments are described above with respect to SP1 and SP2 based systems, which are commercially available from KLA-Tencor, it is to be understood that the configurations of the system embodiments described herein can be implemented on any surface inspection system that utilizes oblique incidence and is responsive to scattered light. In addition, the input beam may be substantially stationary, as in the SP1 and SP2 systems. However, the incident light beam may be scanned using, for instance, an acoustic optic deflector (AOD) preferably with a fast scan length that is small relative to the field of view (FOV) of the collection optics. In this manner, the embodiments described herein may be implemented utilizing any obliquely incident surface scanning dark field optical system. Some additional examples of inspection systems that can be modified as described herein are illustrated in co-pending, commonly assigned U.S. patent application Ser. No. 10/456,203 by Bevis et al. filed Jun. 6, 2003, which is incorporated by reference as if fully set forth herein. The system in which the embodiments described herein are implemented also preferably includes an accessible plane in the collection space such that scattered light may be resolved and blocked as a function of angle as described further herein. In addition, the system in which the embodiments described herein are implemented also includes a processor (e.g., processor 40), which as described above is configured to detect defects on the specimen using signals generated by the detection subsystem.

The inspection system embodiments described herein are configured based on the assumption that the sensitivity of the system is limited by surface or speckle noise. However, inspection system sensitivity may be limited by other noise sources such as shot or thermal noise. Therefore, the system embodiments described herein may be modified to decrease the effect of such noise on the sensitivity of the system. For instance, the system embodiments described herein may be particularly useful when shot-noise limitations can be mitigated, for example, by utilizing a relatively powerful light source such as a laser that emits light having an ultraviolet (UV) wavelength. For example, when a relatively small collection aperture is utilized as described further herein, preferably enough photons are incident on the detector(s) to unambiguously register a sub-wavelength particle or defect. Therefore, illumination of sufficient power is preferably used to illuminate the surface to be inspected. Generally, the power of the light source is preferably as high as possible. However, an appropriate power for the light source may also vary depending on characteristics of the specimen such as defect size and surface roughness and characteristics of the system. In addition, the illumination may have any suitable wavelength known in the art such as, but not limited to, 355 nm, 488 nm, and 532 nm.

The inspection system embodiments described herein are also particularly suitable for inspection of specimens that include films like polysilicon, which generally has short correlation lengths (e.g., small grain size) and limited forward scatter. For example, improved sensitivity to defects having sizes that are lower by about 10% in PSL-equivalent on at least some rougher polysilicon films can be achieved using the systems described herein. Some other rough films like aluminum or copper have relatively large grain sizes with significant forward scatter that tends to compete with the nulls in surface scattering seen in FIG. 2. However, the system embodiments described herein may also be at least somewhat beneficial for inspection of specimens that include such a layer of material. In addition, the systems described herein may have improved sensitivity for small defect detection on high-K and low-K films. Therefore, the level of improvements provided by the embodiments described herein are rather significant since they can be used for inspection of one of the most critical integrated circuit (IC) layers formed during semiconductor manufacturing.

Figure 11:
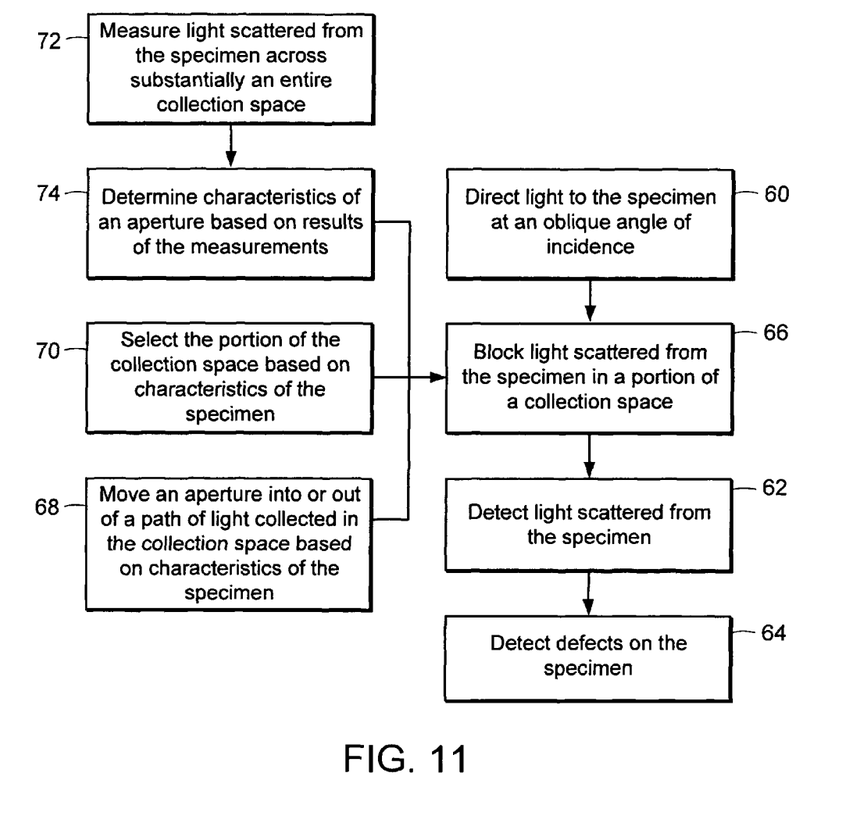
FIG. 11 is a flow chart illustrating one embodiment of a method for inspecting a specimen.

FIG. 11 illustrates one embodiment of a method for inspecting a specimen. It is to be understood that many of the steps shown in FIG. 11 are not essential to practice of the method. In particular, one or more steps may be omitted from or added to the method shown in FIG. 11, and the method can still be practiced within the scope of this embodiment. In addition, many of the steps shown in FIG. 11 do not have to be performed in the order shown in FIG. 11 unless otherwise noted herein.

As shown in step 60, the method includes directing light to the specimen at an oblique angle of incidence. The light is polarized in a plane that is substantially parallel to the plane of incidence. Directing the light to the specimen may be performed as described above. In one embodiment, the specimen includes an uppermost layer having substantial roughness. The specimen may be further configured as described above. The method also includes detecting light scattered from the specimen, as shown in step 62. The detected light is polarized in a plane that is substantially parallel to the plane of scattering. Detecting the light scattered from the specimen may be performed as described further above. In addition, the method includes detecting defects on the specimen using signals responsive to the detected light, as shown in step 64. Detecting the defects may be performed as described herein. In one embodiment, the defects include defects having a size from about 100 nm to about 200 nm. In another embodiment, the defects may include defects having a size that is less than about one half of the wavelength of the light directed to the specimen in step 60.

In one embodiment, the detected light may include the light scattered in only a portion of a collection space containing the plane of scattering. In one such embodiment, a level of the light scattered in the portion is lower than a level of the light scattered in another portion of the collection space. In another such embodiment, the portion includes a portion of two forward scattering quadrants of the collection space. In a preferred embodiment, at least a substantial portion of the detected light includes light that is not scattered by a surface of the specimen.

In some embodiments, the method includes blocking the light scattered in a portion of a collection space containing the plane of scattering, as shown in step 66. In one such embodiment, the light may be blocked in step 66 using an aperture.

The aperture may be configured as described herein. In one such embodiment, the method includes moving the aperture into or out of a path of light collected in the collection space based on characteristics of the specimen, as shown in step 68. The aperture may be moved into or out of the path of the collected light as described further herein. In another embodiment, the method includes selecting the portion of the collection space based on characteristics of the specimen, as shown in step 70. The portion of the collection space may be selected as described further herein (e.g., using the Rice rough surface scatter equations).

In an additional embodiment, the method includes measuring light scattered from the specimen across substantially an entire collection space containing the plane of scattering, as shown in step 72. Measuring the light in step 72 may be performed as described further herein. Such an embodiment may also include determining characteristics of an aperture based on results of the measuring step, as shown in step 74. The characteristics of the aperture may be determined as described further herein. The aperture for which the characteristics were determined in step 74 may then be used to block the light scattered in a portion of the entire collection space, which may be performed as shown in step 66. Each of the embodiments of the method described above may include any other step(s) described herein. In addition, each of the embodiments of the method may be performed using any of the system embodiments described herein.

Further modifications and alternative embodiments of various aspects of the invention may be apparent to those skilled in the art in view of this description. For example, methods and systems for inspecting a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a specimen, comprising:
  an illumination subsystem configured to direct light to the specimen at an oblique angle of incidence, wherein the light is polarized in a plane that is substantially parallel to the plane of incidence;
  a detection subsystem configured to detect light scattered from the specimen, wherein the detected light is polarized in a plane that is substantially parallel to the plane of scattering, and wherein the detection subsystem comprises a polarizing component having a pass axis that is different for different scattering azimuthal angles across the polarizing component such that the polarizing component yields the light that is polarized in the plane that is substantially parallel to the plane of scattering for all scattering angles; and
  a processor configured to detect defects on the specimen using signals responsive to the detected light generated by the detection subsystem.

2. The system of claim 1, wherein the detection subsystem is further configured to detect the light scattered in only a portion of a collection space of the detection subsystem.

3. The system of claim 1, wherein the detection subsystem is further configured to detect the light scattered in only a portion of a collection space of the detection subsystem, and wherein a level of the light scattered in the portion is lower than a level of the light scattered in another portion of the collection space.

4. The system of claim 1, wherein the detection subsystem is further configured such that at least a substantial portion of the detected light comprises light that is not scattered by a surface of the specimen.

5. The system of claim 1, wherein the detection subsystem is further configured to detect the light scattered in only a portion of a collection space of the detection subsystem, and wherein the portion comprises a portion of two forward scattering quadrants.

6. The system of claim 1, wherein the detection subsystem further comprises an aperture configured to block the light scattered in a portion of a collection space of the detection subsystem.

7. The system of claim 1, wherein the detection subsystem further comprises an aperture configured to block the light scattered in a portion of a collection space of the detection subsystem, and wherein the system is further configured to move the aperture into or out of an optical path of the detection subsystem based on characteristics of the specimen.

8. The system of claim 1, wherein the detection subsystem further comprises an aperture configured to block the light scattered in a portion of a collection space of the detection subsystem, and wherein the aperture is selected based on characteristics of the specimen.

9. The system of claim 1, wherein the detection subsystem further comprises an aperture configured to block the light scattered in a portion of a collection space of the detection subsystem, and wherein characteristics of the aperture are determined based on measurements of light scattered from the specimen across substantially an entirety of the collection space.

10. The system of claim 1, wherein the specimen comprises an uppermost layer having substantial roughness.

11. The system of claim 1, wherein the defects comprise defects having a size from about 100 nm to about 200 nm.

12. A system configured to inspect a specimen, comprising:
an illumination subsystem configured to direct light to the specimen at an oblique angle of incidence, wherein the light is polarized in a plane that is substantially parallel to the plane of incidence;
a detection subsystem configured to detect light scattered from the specimen, wherein the detected light is polarized in a plane that is substantially parallel to the plane of scattering, and wherein the detection subsystem comprises a polarizing component having a pass axis that is different for different scattering azimuthal angles across the polarizing component such that the polarizing component yields the light that is polarized in the plane that is substantially parallel to the plane of scattering for all scattering angles; and
a processor configured to detect defects on the specimen using signals responsive to the detected light generated by the detection subsystem, wherein a size of the defects is less than half of a wavelength of the light directed to the specimen.

13. A method for inspecting a specimen, comprising:
directing light to the specimen at an oblique angle of incidence, wherein the light is polarized in a plane that is substantially parallel to the plane of incidence;
detecting light scattered from the specimen, wherein the detected light is polarized in a plane that is substantially parallel to the plane of scattering, wherein said detecting is performed by a detection subsystem, and wherein the detection subsystem comprises a polarizing component having a pass axis that is different for different scattering azimuthal angles across the polarizing component such that the polarizing component yields the light that is polarized in the plane that is substantially parallel to the plane of scattering for all scattering angles; and
detecting defects on the specimen using signals responsive to the detected light.

14. The method of claim 13, wherein the detected light comprises the light scattered in only a portion of a collection space containing the plane of scattering.

15. The method of claim 13, wherein the detected light comprises the light scattered in only a portion of a collection space containing the plane of scattering, and wherein a level of the light scattered in the portion is lower than a level of the light scattered in another portion of the collection space.

16. The method of claim 13, wherein at least a substantial portion of the detected light comprises light that is not scattered by a surface of the specimen.

17. The method of claim 13, wherein the detected light comprises the light scattered in only a portion of a collection space containing the plane of scattering, and wherein the portion comprises a portion of two forward scattering quadrants.

18. The method of claim 13, further comprising blocking the light scattered in a portion of a collection space containing the plane of scattering.

19. The method of claim 13, further comprising blocking the light scattered in a portion of a collection space containing the plane of scattering using an aperture and moving the aperture into or out of a path of light collected in the collection space based on characteristics of the specimen.

20. The method of claim 13, further comprising blocking the light scattered in a portion of a collection space containing the plane of scattering and selecting the portion of the collection space based on characteristics of the specimen.

21. The method of claim 13, further comprising measuring light scattered from the specimen across substantially an entire collection space containing the plane of scattering, determining characteristics of an aperture based on results of said measuring, and blocking the light scattered in a portion of the entire collection space using the aperture.

22. The method of claim 13, wherein the specimen comprises an uppermost layer having substantial roughness.

23. The method of claim 13, wherein the defects comprise defects having a size from about 100 nm to about 200 nm.

* * * * *